United States Patent
Rolley

(10) Patent No.: US 9,213,803 B2
(45) Date of Patent: Dec. 15, 2015

(54) SYSTEM AND METHOD FOR COLLECTING, ANALYZING AND REPORTING FITNESS ACTIVITY DATA

(71) Applicant: David Rolley, Las Vegas, NV (US)

(72) Inventor: David Rolley, Las Vegas, NV (US)

(\*) Notice: Subject to any disclaimer, the term of this patent is extended or adjusted under 35 U.S.C. 154(b) by 0 days.

(21) Appl. No.: 14/268,181

(22) Filed: May 2, 2014

(65) Prior Publication Data

US 2014/0330408 A1 Nov. 6, 2014

Related U.S. Application Data

(60) Provisional application No. 61/818,776, filed on May 2, 2013.

(51) Int. Cl.
*G07F 17/32* (2006.01)
*G06F 19/00* (2011.01)
*G06K 9/00* (2006.01)

(52) U.S. Cl.
CPC ........ *G06F 19/3481* (2013.01); *G06K 9/00288* (2013.01); *G06K 9/00342* (2013.01)

(58) Field of Classification Search
USPC ................................................. 700/91; 482/9
See application file for complete search history.

(56) References Cited

U.S. PATENT DOCUMENTS

| | | | |
|---|---|---|---|
| 4,907,795 A | 3/1990 | Shaw et al. | |
| 6,656,091 B1 | 12/2003 | Abelbeck et al. | |
| 6,746,371 B1* | 6/2004 | Brown et al. | 482/8 |
| 2004/0077462 A1* | 4/2004 | Brown et al. | 482/8 |
| 2005/0075214 A1* | 4/2005 | Brown et al. | 482/8 |
| 2006/0252602 A1* | 11/2006 | Brown et al. | 482/9 |
| 2011/0115609 A1 | 5/2011 | Gordon | |
| 2013/0053218 A1 | 2/2013 | Barker | |

OTHER PUBLICATIONS

International Search Report and Written Opinion; PCT/US2014036603; Sep. 9, 2014.

\* cited by examiner

*Primary Examiner* — Pierre E Elisca
(74) *Attorney, Agent, or Firm* — Howard & Howard Attorneys PLLC

(57) ABSTRACT

In one aspect of the invention, a system for monitoring a fitness activity of user performing a fitness activity with an exercise device is described herein. The system includes a sensor for sensing and transmitting data indicative of an exercise that is being performed with an exercise device, a user identification device, a database, and a processor. The processor is configured to receive a signal indicative of a patron ID and responsively retrieve a patron record being associated with the received patron ID from the database. The processor also determines a planned exercise sequence associated with the patron exercise session as a function of the retrieved patron record, determines a current exercise sequence being performed by the patron, and determines a condition of the patron exercise session as a function of the planned exercise sequence and the current exercise sequence.

20 Claims, 10 Drawing Sheets

Planned Exercise Session — 82, 88

| Exercise Type | Weight | No. Sets | No. Reps | Tempo | Rest |
|---|---|---|---|---|---|
| Bench Press | 200lbs | 4 | 6 | 1 sec/rep | 2 min. |
| Lunges | 20lbs | 6 | 6 | 2 sec/rep | 1 min. |

Figure 7

Fitness Activity
Exercise Session: Bench press — 90

| Session | Weight | No. Sets | No. Reps | Tempo | Rest |
|---|---|---|---|---|---|
| Current | 185 lbs | 4 | 8 | 2.5 sec/rep | 3 min. |
| Planned | 200 lbs | 4 | 8 | 1 sec/rep | 2 min. |

Total Effort: 90%

Figure 8

SYSTEM AND METHOD FOR COLLECTING, ANALYZING AND REPORTING FITNESS ACTIVITY DATA

CROSS REFERENCE TO RELATED APPLICATION

This application claims the benefit of U.S. Provisional Patent Application Ser. No. 61/818,776, filed May 2, 2013, the disclosure of which is hereby incorporated by reference in its entirety for all purposes.

TECHNICAL FIELD

The invention generally relates to systems and methods for collecting, analyzing and reporting fitness activity data, such as data relating to muscle mechanics, among other things.

BACKGROUND

The public is becoming ever increasingly aware of their individual physical fitness needs. There exists a wide variety of training advice and fitness regimens for the public to follow, which may be customized to suit individual preferences and limitations. There also exists devices that may be used to track fitness efforts, such as pedometers.

It would be useful if a system and method were developed which could measure physical parameters and, from those measurements, determine the impact of an individual's fitness training efforts for the purpose of providing feedback and guidelines to assist in improving that individual's fitness training efforts and managing the risk of potential injury.

The present invention is aimed at one or more of the problems identified above.

SUMMARY OF THE INVENTION

The invention is generally directed to systems and methods for monitoring a fitness activity of a user performing an exercise.

In one aspect of the invention, a system for monitoring a fitness activity of a user performing a fitness activity with an exercise device is provided. The system includes a sensor that is adapted to be coupled to the exercise device for sensing and transmitting data indicative of an exercise that is being performed with the exercise device, a user identification device for use in identifying a patron ID, a database, and a processor. The database includes a collection of patron records. Each patron record is associated with a corresponding patron ID and includes a list of patron exercises. The processor is configured to receive, from the sensor, a signal indicative of a force being applied to the exercise device and responsively initiate a patron exercise session and receive, from the user identification device, a signal indicative of a patron ID and responsively retrieve a patron record being associated with the received patron ID from the database. The processor also determines a planned exercise sequence associated with the patron exercise session as a function of the retrieved patron record, determines a current exercise sequence being performed by the patron with the exercise device as a function of the sensed force being applied to the exercise device, and determines a condition of the patron exercise session as a function of the planned exercise sequence and the current exercise sequence.

In another aspect of the invention, an apparatus for monitoring a fitness activity of user performing a fitness activity is provided. The apparatus includes an exercise device for use in performing the fitness activity by the user, a sensor coupled to the exercise device for sensing and transmitting data indicative of a fitness activity being performed with the exercise device, a user identification device for use in identifying a patron ID, a database, and a processor. The database includes a collection of patron records. Each patron record is associated with a corresponding patron ID and includes a list of patron exercises. The processor is configured to receive, from the sensor, a signal indicative of a force being applied to the exercise device and responsively initiate a patron exercise session, and receive, from the user identification device, a signal indicative of a patron ID and responsively retrieve a patron record being associated with the received patron ID from the database. The processor also determines a planned exercise sequence associated with the patron exercise session as a function of the retrieved patron record, determines a current exercise sequence being performed by the patron with the exercise device as a function of the sensed force being applied to the exercise device, and determines a condition of the patron exercise session as a function of the planned exercise sequence and the current exercise sequence.

In yet a further aspect of the invention, a method of monitoring a fitness activity of a user performing a fitness activity with an exercise device is provided. The method includes the steps of receiving, by a processor, a signal indicative of a force being applied to the exercise device and responsively initiating a patron exercise session, and receiving, from the user identification device, a signal indicative of a patron ID and responsively retrieving a patron record being associated with the received patron ID from a database. The method also includes determining, a planned exercise sequence associated with the patron exercise session as a function of the retrieved patron record, determining a current exercise sequence being performed by the patron with the exercise device as a function of the sensed force being applied to the exercise device, and displaying a trace indicative of the planned exercise sequence and the current exercise sequence on a display device.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 7-12 are graphical displays of a fitness activity that may be displayed with the monitoring system shown in FIG. 1, according to an embodiment of the present invention;

DETAILED DESCRIPTION OF THE INVENTION

Figure 1:
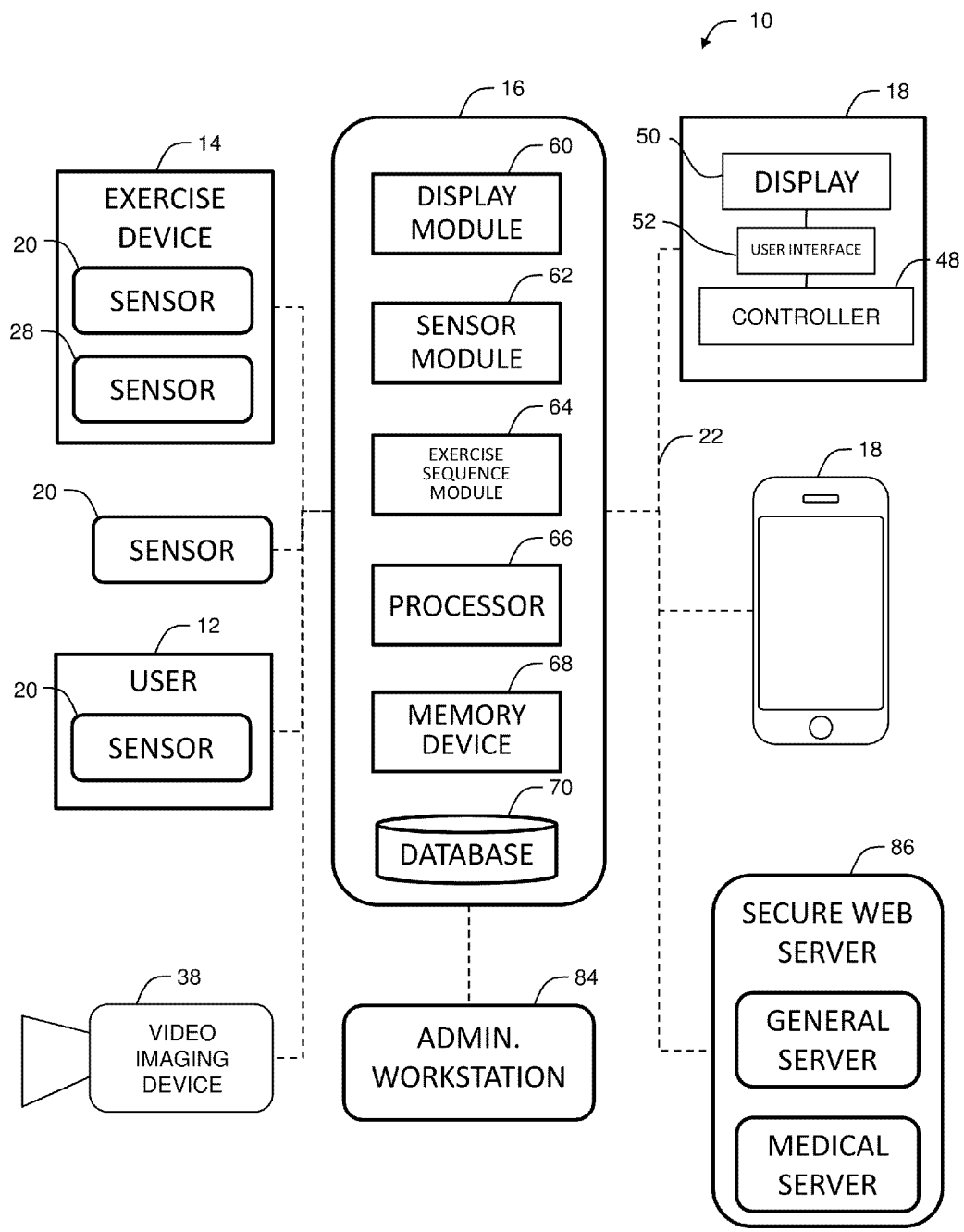
FIG. 1 is a block diagram of an exemplary monitoring system that may be used to monitor a fitness activity of a user performing an exercise with an exercise device, according to an embodiment of the present invention.

The invention is generally directed to systems and methods for, among other things, monitoring a fitness activity of a user performing an exercise, providing feedback and guidelines to assist in improving an individual's fitness training efforts and managing the risk of potential injury.

Some embodiments of the invention include systems and methods which provide for collecting and/or receiving a plurality of individual fitness activity data, which may include data relating to the individual's musculature response to exertion and body mechanics, among other things; analyzing the fitness activity data to determine trends and baseline profile information; comparing additional fitness activity data with the determined trends and baseline profile information; and reporting the data or providing an alert if the additional fitness activity data does not conform to the determined trends and baseline information or is outside preset threshold values.

In some embodiments, a statistical probability algorithm is used to analyze the fitness data and compare additional fitness data.

A system of the invention may provide user interfaces configured as graphical user interfaces (also referred to herein as "screens") which may be presented on a display. Graphical user interfaces which may be employed may generally incorporate user-friendly features and fit seamlessly with other operating system interfaces, that is, in a framed form having borders, multiple folders, toolbars with pull-down menus, embedded links to other screens and various other selectable features associated with animated graphical representations of depressible buttons. These features can be selected (i.e., "clicked on") by the user via connected mouse, keyboard, or other commonly used tool for indicating a preference in a computerized graphical interface.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Those skilled in the art will also readily appreciate that systems and methods configured in accordance with the invention including the exemplary embodiment in the accompanying materials may include or employ various computer and network related software and hardware, such as software and hardware which are used in a distributed computing network, that is, programs, operating systems, memory storage devices, input/output devices, data processors, servers with communication links, wireless or otherwise, such as those which take the form of a local or wide area network, and a plurality of data terminals within the network, such as personal computers and mobile devices. Those skilled in the art will further appreciate that, so long as its users are provided with access to systems and methods constructed in accordance with the invention, specific types of network, software or hardware are not vital to its implementation.

In some embodiments, a processor, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

In some embodiments, a database, as described herein, includes any collection of data including hierarchical databases, relational databases, flat file databases, object-relational databases, object oriented databases, and any other structured collection of records or data that is stored in a computer system. The above examples are exemplary only, and thus are not intended to limit in any way the definition and/or meaning of the term database, in that any database may be used that enables the systems and methods described herein.

Some embodiments of the invention are also directed to a non-transitory machine readable media for providing methods as described herein, including one or more software programs, code and/or data segments as necessary to install or otherwise provide any of the methods described herein on one or more computing machines.

These and other aspects of the systems and methods of the invention will become more readily apparent to those having ordinary skill in the art from the following description of an exemplary embodiment of the invention taken in conjunction with the exemplary embodiment of the methods and systems of the invention as described herein.

An exemplary embodiment of the invention provides a system for connecting all equipment in a facility (where applicable) for a total body holistic approach. Algorithms used will be able to help predict potential injury if the client uses our product/equipment and system for working out.

In some embodiments, systems and components may be designed around some or all of the following features: performance training: meaning optimized training to perform in any sport or daily activity; early detection of injury through trending of data and analyzing activities; secure HIPAA data for the medical side of business; secure personal information via a customized "Smartband" used in some embodiments of the invention which also houses individual medical information in case of emergency or for doctors records; algorithms that take pre-stored data and information to provide strong results and predictive progress based off either baseline profile or baseline with past history analysis; multiple facilities can connect across the network to integrate multiple fitness and/or medical facilities; and FCC licensed wireless network platforms.

Data is trended over time such that progress can be predicted by some embodiments of the invention. The invention can be configured to store data trends in the knowledge base and offer adjustments to workout per specific sport, and provide ongoing support routines to provide a holistic approach to training. For example different sports require different muscles and movements, without the foundation of support muscle for those movements and muscle groups. There is a chain reaction effect which can be detected and mitigated by this embodiment of the invention.

Some of the data captured by embodiments of the invention may include but is not limited to the following:
 a. Exercise Performed
 b. Range of Motion
 c. Duration of Repetition
 d. Duration of Set
 e. Number of Repetitions
 f. Number of Sets
 g. Tempo of Repetitions
 h. Total Effort i. Average Effort
j. Peak Concentric Force
k. Average Concentric Force
l. Peak Eccentric Force
m. Average Eccentric Force Depending on the training requirements routines that are established, the system of the invention can notify trainers and patrons that the lack of either fast twitch muscles or slow twitch muscles are not being balanced in the current routine and history.

The system of the invention may also advantageously be used in larger facilities to locate personnel in case of an emergency.

Due to the electronics attached, the system of the invention may also advantageously be used so that each piece of equipment can now have an associated unique ID such as an IP address, which can be used in maintenance programs for scheduling maintenance, analyze usage of the equipment so that the facility can remove equipment that is never used to allow a smaller foot print or only carry the equipment that is utilized within the facility.

The system of the invention may also provide for social media connections, so that users can connect with friends or competitors across the country or work out at the same time at a different gym, synchronize workouts and compare progress.

In some embodiments, the system and/or equipment recognizes an individual, accesses the individual's profile and records, stores fitness activity data relating to the current workout and updates trends relating to the individual's workouts in a database. Information is compared to beginning profile and baseline profile and areas of improvement or no improvement highlighted over time. Real time data immediately available through the system of the invention.

Systems of the invention permit personal trainers to function remotely as a person performs exercises, data is received and the trainers can communicate with the individual, for example, through text messages. Trainers can thus adjust the work out for many while staying in his/her office or remote location.

The invention provides records of muscle mechanics to provide to physical therapists or an attending physician upon completion of a rehab session. Rehab patients can view their progress instantly and review on a weekly basis with physician (i.e. cardiologist or physical therapist etc).

It should be understood that the system of the invention may incorporate any exercise and machine or weights, such as treadmill, stair climbers, and elliptical equipment. Free weights for use with the system of the invention may have electronics built inside or attached, which will also allow the system to identify each weight as part of the system.

The system also enables communications for hand off to predetermined routines or check availability. Each piece of equipment may include a digital communication unit for enabling equipment to equipment or peer to peer communication for system self healing in case of failure of equipment communication at any given point in time. The system allows individual end users to be able to go to a system website or through the fitness center's website to view their progress. The system may also conduct a macro-analysis of the fitness center data and, based on the normal use patterns, compare to the individual's predetermined work out and provide them with the best time to go work out.

Figure 2:
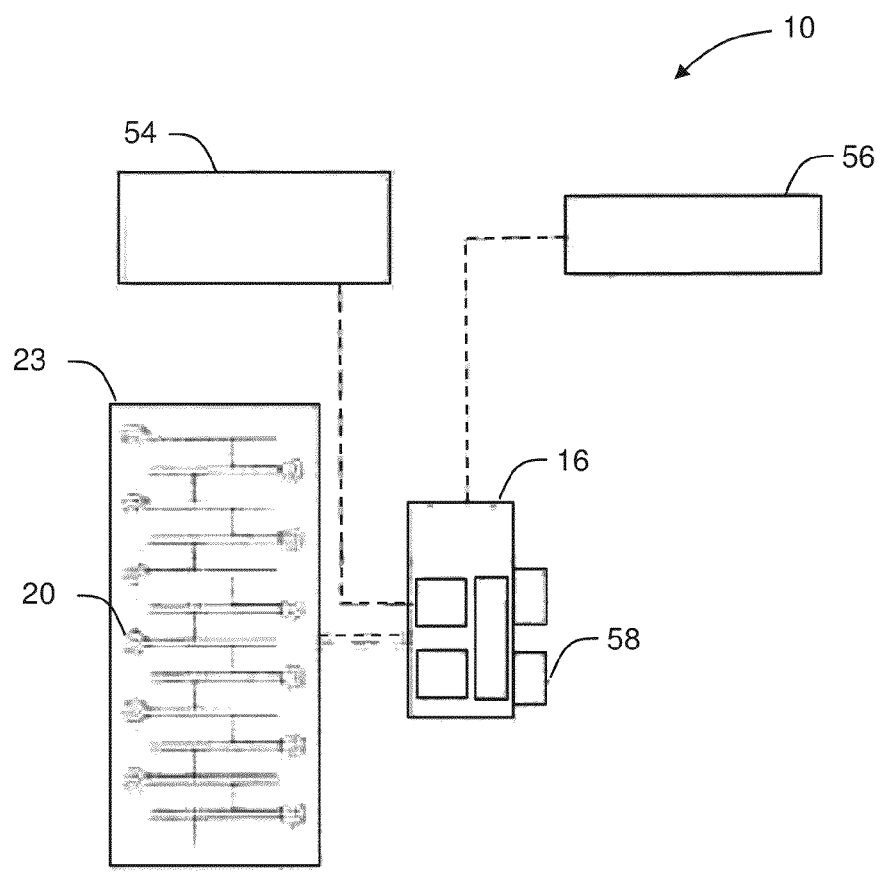
FIG. 2 is a block diagram of a computing device that may be used with the monitoring system shown in FIG. 1, according to an embodiment of the present invention.

As shown in the accompanying figures, including FIG. 1 which provides a schematic diagram showing a general system overview, and FIG. 2 which provides a diagram of a bench press with weight sensor, which may be used with embodiments of the invention. Sensors may be strategically located within the equipment or attached, or otherwise be associated with the equipment and have multiple configurations dependent on the intended use. For example in training on free weight equipment a flat bench can be used for many exercises. Based on the exercise preconfigured in the users program or the weight distribution the attached electronic digital communication unit determines the exercise being performed. Sensors may include any conventional sensors for detecting and recording movement, among other things, including video cameras or movement capturing cameras for detecting physical movement.

Figure 3:
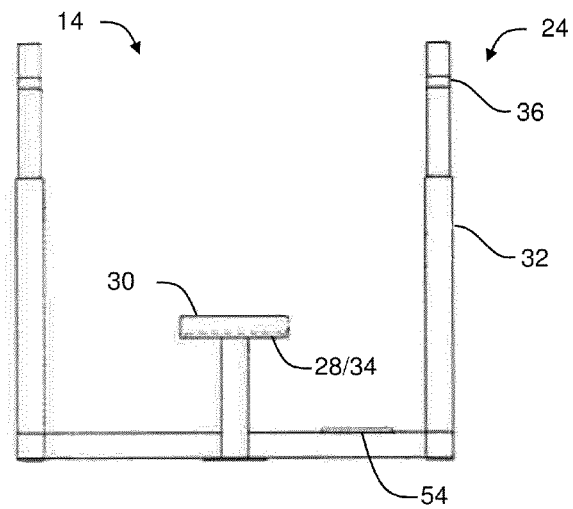
FIGS. 3-5 are schematic views of an exercise device that may be used with the monitoring system shown in FIG. 1, according to an embodiment of the present invention.
Figure 4:
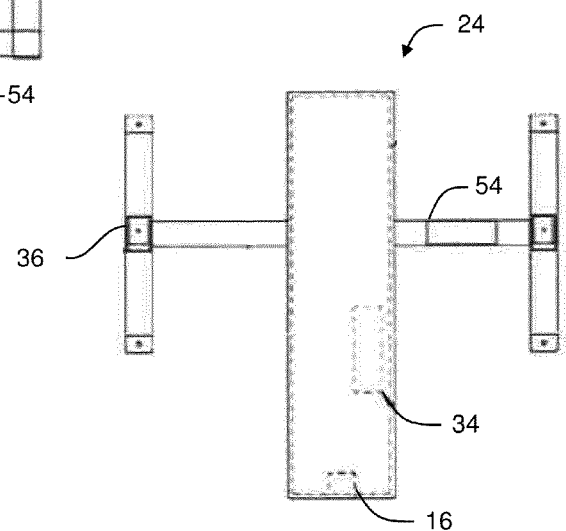
Figure 5:
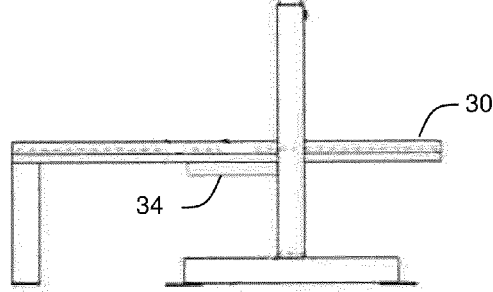
Figure 15:
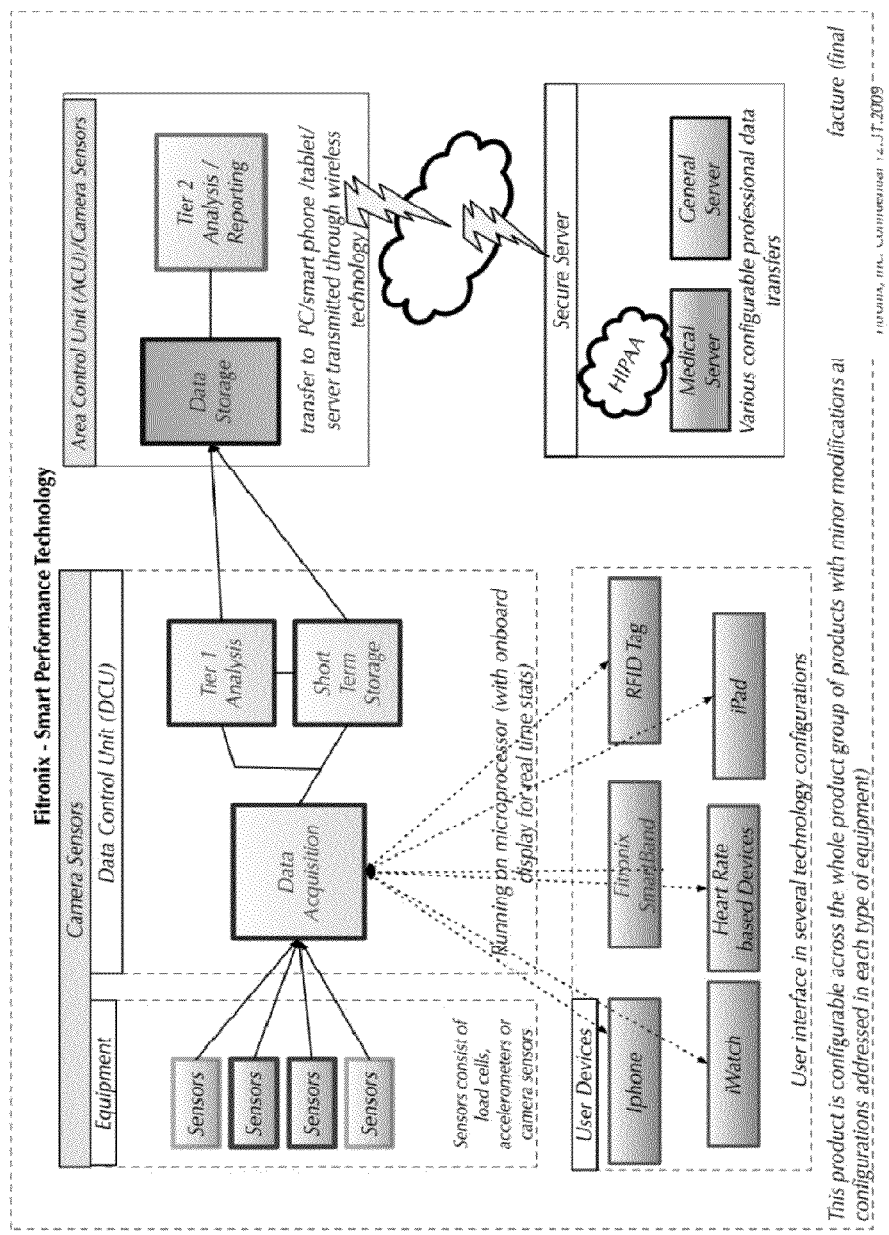
FIG. 15 is another block diagram of the monitoring system shown in FIG. 1, according to an embodiment of the present invention.

FIGS. 1 and 15 are block diagrams of an exemplary monitoring system 10 that may be used to monitor a fitness activity of a user 12 performing an exercise with an exercise device 14. FIG. 2 is a block diagram of a computing device 16 that may be used with the monitoring system 10. FIG. 3 is front view of an exercise device 14 that may be used with the monitoring system 10. FIG. 4 is a top view of an exercise device 14 shown in FIG. 3, and FIG. 5 is a side view of the exercise device 14 shown in FIG. 3.

In the illustrated embodiment, monitoring system 10 includes a user identification device 18, a computing device 16 that is coupled in communication with the user identification device 18, and one or more sensors 20 that communicate with the computing device 16 for detecting various parameters relative to a fitness activity being performed by a user 12. In the illustrated embodiment, the monitoring system 10 may be used to monitor a patron exercise session being performed by a user/patron 12 including a plurality of exercises being performed using a plurality of exercise equipment in a gym. In addition, in one embodiment, the system 10 may be configured in a portable manner for offsite evaluation and outside training.

The computing device 16 communicates with the sensors 20 and/or the user identification devices 18 via a communications link 22 such as, for example, the Internet, a cellular telecommunications network, a wireless network and/or any suitable communications network that enables the computing device 16 to access the sensors 20 and/or the user identification devices 18.

The computing device 16 receives data indicative of the fitness activity being performed by the user and determines a current fitness activity level of the user based on the sensed data. In addition the computing device 16 compares the current fitness activity level with a planned activity level and determines a condition of a user exercise session based on a difference between the current and planned activities levels. Moreover, the computing device 16 may display the current and/or planned activity levels to the user to allow the user to view any current differences and/or deviations from the planned activity level.

In one embodiment, the system 10 may generate a current exercise sequence and/or a current fitness activity level and compare the sequence and/or activity level to either a planned exercise sequence and/or a history of the sequences that have been performed by the patron/athlete. The system 10 may also transmit messages indicative of the current exercise sequence and/or a current fitness activity level to a plurality of user identification device 18 and/or display the information on a website to notify trainers, medical practitioners and patron or any suitable user of current exercise sequences, current fitness activity levels, planned exercise sequences/levels and/or historic sequences/levels associated with the patron/athlete.

The sensors 20 may include, but are not limited to, motion sensors, vibration sensors, position sensors, temperature sensors, acceleration sensors, speed sensors, load sensors, load cells, weight sensors and/or any other sensors that sense various parameters relative to the performance of an exercise and/or fitness activity being performed by a user. The monitoring system 10 may also include sensors that may be contained within the pad of the exercise equipment. The monitoring system 10 may also include a sensor pad 23 (shown in FIG. 2) that is coupled to the exercise device 14. The sensor pad 23 may include a plurality of sensors 20 for sensing a position and/or weight distribution of the patron/athlete positioned on the exercise device 14.

In one embodiment, the monitoring system 10 includes at least one sensor 20 that is coupled to an exercise device 14 for sensing fitness parameters associated with an exercise being performed by the user with the exercise device 14. The exercise device 14 may include, but is not limited to, a weight bench 24 (shown in FIGS. 3-5), an exercise mat 26 (shown in FIG. 14), a bench, a squat rack, a weight rack, a treadmill, a stationary bicycle, a pilates reformer, free weights, a cable machine, a rowing machine, an elliptical machine, a multi-station machines, personal/home gym systems, and/or any suitable exercise equipment that enables the monitoring system 10 to function as described herein. In addition, the monitoring system 10 may include at least one sensor 20 that is coupled to the patron 12.

For example, in one embodiment, the system 10 may include wearable sensors that can be attached to the body or is contained within a particular material worn as clothing or an attachment to the attire of the patron. In addition, the system 10 may include a portable EEG system that attaches and provides ongoing data of the frequency of the brain waves prior to/during and after training sessions. The EEG sensors are tied to a separate algorithm that interrogates the brain waves and provides a definitive assessment of the emotions/behavior of the athlete/person, and is included in the overall real time assessment of the activities. The EEG systems may also be used to sense fitness activity during use in actual sporting events. In addition, the system 10 may also include hand scanning sensors that may be used to scan the content of particular vitamins and nutrients mainly used to accurately determine and identify the level of deficiency of vitamins within the body at training time and after training. Through the algorithm determines the exhaustion pattern of absorbed vitamins to determine a level of hormone levels in the patron and identify those using to adjust the algorithm and run a separate predictive baseline, etc.

In addition, in one embodiment, the system 10 enables synchronization of the data across the multiple devices or the system to synchronize the data flow from multiple sources. Information that may be obtained by the system 10 includes, but is not limited to, ECG/EKG data, Heat flux—to measure rate at which heat is dissipating-perspiration, Skin temperature, GPS for location of body extremities and skeletal structure, EEG data, BMI, Muscle Tone, Stance Posture, and/or Biomechanics of each exercise.

In one embodiment, the system 10 includes three sensing layers to enable the computing device 16 to determine decides which is the most accurate for the calculations and data feedback: Layer one—motion capture video, Layer two—equipment sensors, and Layer three—wearable sensor.

In the illustrated embodiment, the monitoring system 10 includes at least one load sensor 28 that is coupled to the exercise device 14 such as, for example, the weight bench 24, for sensing a load being imparted on the exercise device 14 by the user, and transmitting data indicative of the sensed load to the computing device 16. The weight bench 24 may include a bench 30 and a weight rack 32 that is coupled to one end of the weight bench 24. The system 10 may include a first load sensor 34 that is coupled to the bench 30 for sensing a load being imparted to the bench 30, and a second load sensor 36 that is coupled to the weight rack 32 for sensing a load being imparted to the weight rack 32.

Referring to FIGS. 3-5 and 13, during an exercise session being performed with the weight bench 24, as a patron 12 places a lifting bar and weights on the weight rack 32, the second load sensor 36 detects the load being imparted onto the weight rack 32 from the lifting bar and weights and transmits a signal indicative of the sensed load to the computing device 16. In addition, as the patron contacts the bench 30 to begin an exercise, e.g. lays on the bench to perform a set of bench press repetitions, the first load sensor 34 detects the load being imparted on the bench 30 by the patron and transmits a signal indicative of the sensed load to the computing device 16. Moreover, the first and the second load sensors 34 and 36 may also detect a change in the sensed loads during the performance of the exercise by the patron. For example, as the patron lifts the weight from the weight rack 32, the first and second load sensors 34 and 36 detect a change in the loads being imparted to the bench 30 and the rack 32, respectively. In addition, as the patron lowers and raises the weight to perform a repetition (shown in FIG. 13), the first load sensor 34 detects a change in load being applied to the bench 30 as the weight is lowered and raised by the patron 12.

Figure 14:
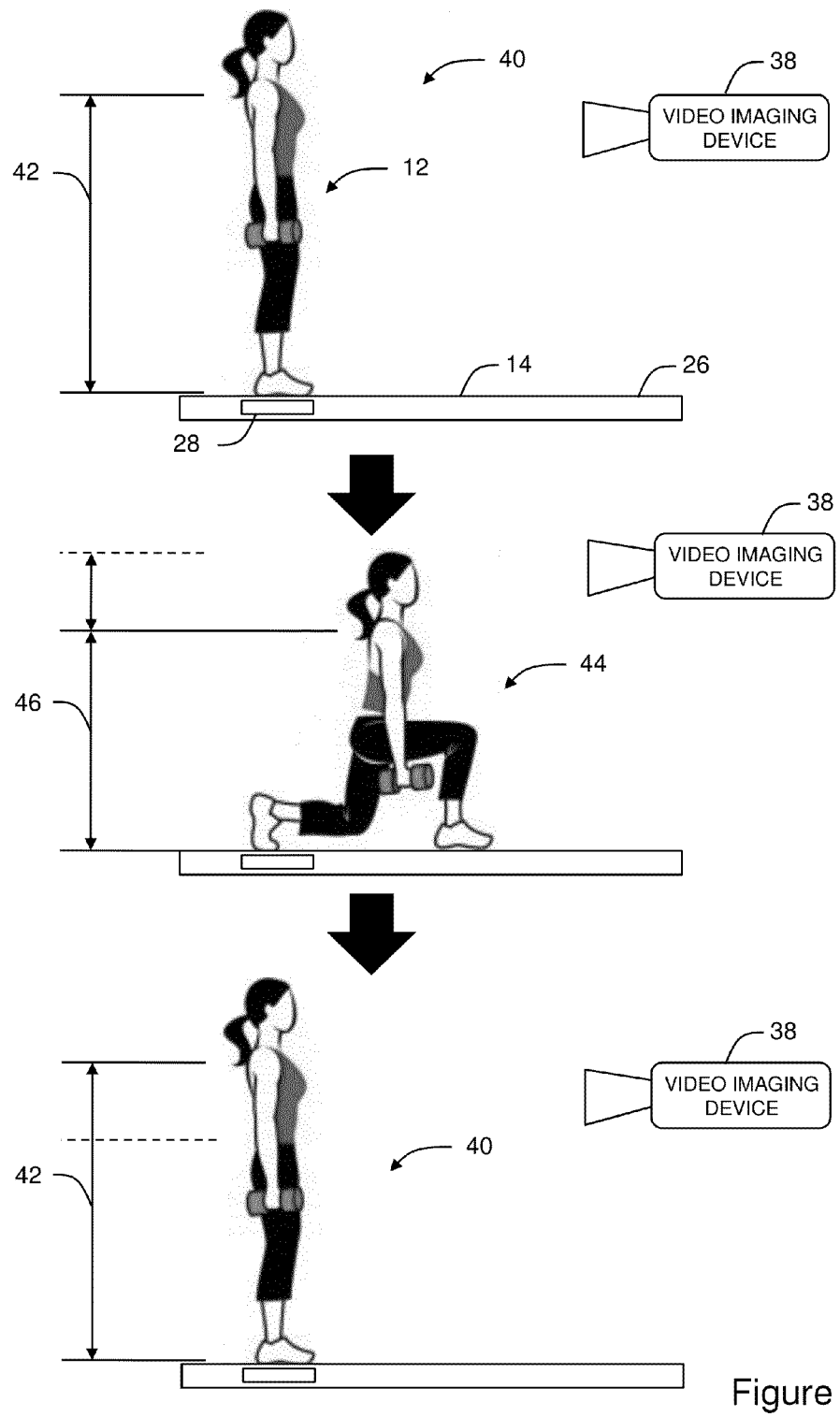

In the illustrated embodiment, the system 10 may also include a video imaging device 38 such as, for example, a video camera that is configured to capture and transmit images of a patron performing a fitness activity to the computing device 16. In addition, the video imaging device 38 may be configured to detect a position of a patron and/or portions of the patron's body during the performance of an exercise for use in determining a range of motion during the exercise. For example, as shown in FIG. 14, during a lunge exercise, the video imaging device 38 may detect a first position 40 of a patron including a first height 42 of the patron above an exercise mat 26. During the exercise, as the patron extends forward and lowers towards the mat, the video imaging device 38 may detect a second position 44 of the patron's body including a second height 46 of the patron above the exercise mat 26 and transmit the sensed data to the computing device 16. In one embodiment, the system 10 may include a load sensor 28 that is coupled to the exercise mat 26 for sensing a change in the load being applied to the mat 26 by the patron. For example, during the lunge exercise, the load sensor 28 may detect a change in the load being applied to the mat 26 as the patron extends forward to perform a lunge repetition.

The video imaging device 38 may also include a motion-capture device for generating data indicative of motion-capture video images. The video imaging device and sensors, in some embodiments, may be incorporated to devise a sub-system in specific requirements in sports training. For instance in soccer in learning to properly strike the ball a hypersensitive sensor may be enclosed within the ankle region to capture vibrations while the video motion capture allows visibility to the biomechanics of the task. The system 10 may also use motion capture video to generate and store images of normal activities being performed by the athlete/patron such as walking, running, and/or aerobic exercises and flag these images for review by professional for purposes of evaluating normal balance or over compensation of an injury.

The user identification device 18 is coupled in communication with the computing device 16 to transmit and receive data to and/or from the computing device 16 to enable a user to interact with the computing device 16 to view, input, and/or modify information associated with a fitness activity, health, and/or exercise being performed by the user. In the illustrated embodiment, the user identification device 18 includes a controller 48 that is coupled to a display device 50 and a user interface device 52. The controller 48 receives and transmits information to and from the computing device 16 and displays graphical interfaces (shown in FIGS. 7-12) on the display device 50 to enable the user to interact with the computing device 16. In one embodiment, the user interface device 52 may include, without limitation, a keyboard, a keypad, a touch-sensitive screen, a scroll wheel, a pointing device, a barcode reader, a magnetic card reader, a radio frequency identification (RFID) card reader, an audio input device employing speech-recognition software, a camera, a facial recognition device, a biometric reader, a motion-capture device, a video capture device, and/or any suitable device that enables a user to input data into the controller 48 and/or to retrieve data from the controller 48. The display device 50 may include, without limitation, a flat panel display, such as a cathode ray tube display (CRT), a liquid crystal display (LCD), a light-emitting diode display (LED), active-matrix organic light-emitting diode (AMOLED), a plasma display, and/or any suitable visual output device capable of displaying graphical data, video images, and/or text to a user. In one embodiment, a single component, such as a touch screen, a capacitive touch screen, and/or a touchless screen, may function as both the display device 50 and as the user interface device 52. The user identification device 18 may also include, but is not limited to, personal computers, portable devices such as, for example, tablet computers, cellular phones, smart phones, wearable computing devices such as smart watches and/or smart bands (e.g. Fitbit®), and/or other devices such as game consoles and/or interactive or smart televisions. In one embodiment, the user identification device 18 may also include one or more sensors 20 that are coupled to the controller 48 for detecting information indicative of a fitness activity being performed by the user. The controller 48 may transmit the sensed data to the computing device 16. For example, in one embodiment, the user identification device 18 may include an accelerometer and/or a position sensor for use in sensing a movement of the user during performance of a fitness activity.

In one embodiment, the monitoring system 10 may also include a display unit 54 that is coupled to the computing device 16, a rechargeable battery pack 56 for providing power to the display unit 54, sensors 20, and/or computing device 16, and a communications device 58 that is configure to communicate with the sensors 20, display unit 54, and/or user identification device 18 via wireless communication such as, for example, via Bluetooth® wireless technology. The display unit 54 may include a user interface device 52 and/or a display device 50 for use in displaying the graphical interfaces.

In the illustrated embodiment, the computing device 16 includes a display module 60, a sensor module 62, an exercise sequence module 64, a processor 66, a memory device 68, and a database 70. The processor 66 is coupled in communication with the memory device 68 for executing programmed instructions stored in memory device 68 to control components of the computing device 16, sensors 20, and/or user identification device 18. The processor 66 in particular executes programmed instructions to enable the system 10 to generate and store information indicative of exercise programs being performed by a user and/or fitness activities planned and performed by the user. Moreover, the memory device 68 stores and retrieves information in the database 70 including, but not limited to, image data for producing images and/or screens on the user identification device 18, and temporarily stores variables, parameters, and the like that are used by the processor 66.

The database 70 contains information on a variety of matters, such as, for example, patron records including information associated with a plurality of patrons, unique patron identification (ID) numbers associated with each patron record, fitness activities, exercise device types, exercise sequences, exercise values associated with exercise sequences. The exercise values associated with each exercise sequence includes, but is not limited to, a number of exercise sets, a number of exercise repetitions included in each exercise set, time to complete each exercise repetition, time between each repetition and/or tempo of exercise repetitions, time to complete each set, time between each set, range of motion, total effort, an average effort, a peak concentric force, an average concentric force, a peak eccentric force, and/or an average eccentric force.

The sensor module 62 communicates with each sensor 20 for transmitting and receiving information from each sensor 20. For example, each sensor 20 may transmit a signal corresponding to a sensed fitness parameter of a fitness activity being preformed by the user. Each sensor 20 may transmit a signal continuously, periodically, or only once and/or any other signal timing that enables computing device 16 to function as described herein. Moreover, each sensor 20 may transmit a signal either in an analog form or in a digital form.

In the illustrated embodiment, the exercise sequence module 64 receives data indicative of a fitness activity being performed by the user and generates a current exercise sequence as a function of the received data. In addition, the exercise sequence module 64 may compare the current exercise sequence with a planned exercise sequence associated with the patron and determine a condition and/or quality of the patron's fitness activity based on the current and planned exercise sequences. For example, in one embodiment, the exercise sequence module 64 may determine the condition of the patron exercise session to be less than a predefined exercise session if the current exercise sequence is different from the planned exercise sequence. In addition, the exercise sequence module 64 may determine a plurality of exercise values being associated with the current exercise session based on the sensed data being received from the sensors. For example, in one embodiment, the exercise sequence module 64 may determine exercise values including, but not limited to, a number of exercise sets performed, a number of exercise repetitions in each exercise set, a time to complete each exercise repetition, a tempo of exercise repetitions, a time to complete each set, a time between each set, a range of motion during each repetition, a total effort, an average effort, a peak concentric force, an average concentric force, a peak eccentric force, and/or an average eccentric force.

The display module 60 is configured to display various images on the display device 50 and/or the display unit 54 preferably by using computer graphics and image data stored in the database 70. In the illustrated embodiment, the display module 60 displays information indicative of a fitness activity being performed by the patron including exercise sequence data being generated by the exercise sequence module 64. In the illustrated embodiment, the display module 60 generates and displays a plurality of traces 72 that corresponding to data indicative of the current exercise sequence 74 and the planned exercise sequences 76 (shown in FIGS. 9 and 10) determined by the exercise sequence module 64. In addition, the display module 60 may generate and display traces 72 corresponding to data indicative of a current range of motion 78 and a planned range of motion 80 (shown in FIGS. 11 and 12)

determined by the exercise sequence module 64. Moreover, as shown in FIGS. 7 and 8, the display module 60 may display information indicative of an exercise session including a type of exercise being performed including associated exercise values 82, and data indicative of the current exercise sequence 74 and the planned exercise sequence 76 including associated exercise values 82 determined by the exercise sequence module 64.

In one embodiment, the system 10 may also include one or more administrator workstations 84 that are connected to the computing device 16 to enable an administrative user to access the computing device 16 to transmit data indicative of the planned fitness activities to the computing device 16. This enables an administrative user such as, for example, a personal trainer and/or gym manager, to periodically view and/or update information included in a patron record including exercise sessions, planned exercise sessions, and/or any suitable information.

In addition, in one embodiment, the computing device 16 may transmit information to a secured web server 86 to provide information related to a patron's fitness activity to a third party, such as, for example, a health care professional and/or a personal trainer.

Figure 6:
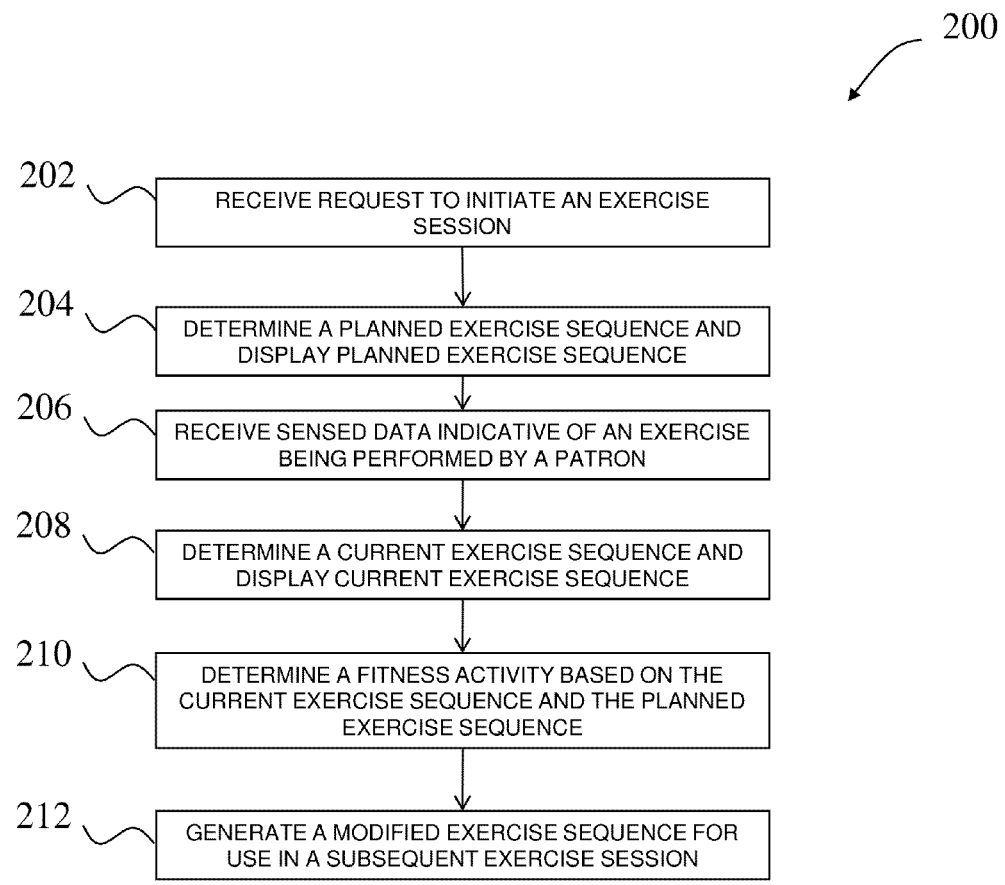
FIG. 6 is a flowchart of a method that may be used with the monitoring system shown in FIG. 1 for monitoring a fitness activity of a user performing an exercise with an exercise device, according to an embodiment of the present invention.
Figure 13:
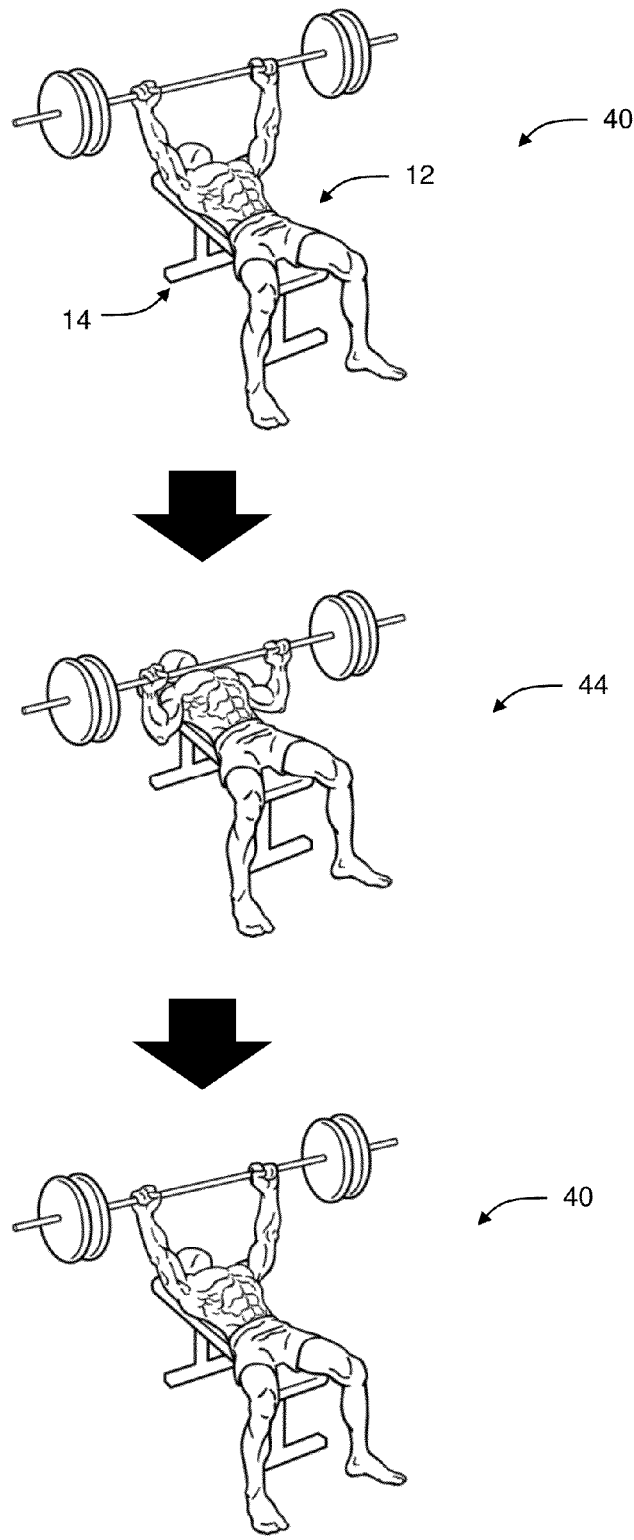
FIGS. 13 and 14 are graphic illustrations of exercises that may be performed with the monitoring system shown in FIG. 1, according to an embodiment of the present invention.

FIG. 6 is a flowchart of a method 200 that may be used with the monitoring system 10 for monitoring a fitness activity of a patron 12 performing an exercise with an exercise device 14. Each method step may be performed independently of, or in combination with, other method steps. Portions of the method 200 may be performed by any one of, or any combination of, the components of the system 10. FIGS. 7-12 are graphical displays of a fitness activity that may be displayed with the monitoring system 10. In the illustrated embodiment, graphical displays are presented via the display device 50 and/or the display unit 54 (shown in FIGS. 1 and 2) and may receive input (e.g., selections and/or entries) via the user identification device 18 and/or the display unit 54. FIGS. 13 and 14 are graphic illustrations of exercises that may be performed by the patron 12 with the monitoring system 10.

In the illustrated embodiment, in method step 202, the computing device 16 receives a request from a patron to initiate an exercise session. In one embodiment, user identification device 18 may transmit a signal indicative of a unique patron ID to the computing device 16 via a wireless communication link. The computing device 16 may receive the patron ID and responsively retrieve the corresponding patron record from the database 70. In addition, the computing device 16 may receive a signal indicative of a patron's use of an exercise device 14 and responsively initiate an exercise session. For example, the computing device 16 may receive a signal indicative of a force being applied to the exercise device 14 from a load sensor 28 and responsively initiate an exercise session upon receiving the sensed load. In one embodiment, the computing device 16 may display a login screen (not shown) on the user identification device 18 and/or the display unit 54 to request the unique patron ID such as, for example, requesting a username and/or password. In one embodiment, the unique patron ID may also include a unique biometric signature (e.g. thumbprint, DNA) and/or facial recognition.

In method step 204, the computing device 16 determines a planned exercise sequence associated with the exercise session and displays information indicative of the planned exercise sequence on the display device 50 and/or the display unit 54. For example, the computing device 16 may display a planned exercise session screen 88 (shown in FIG. 7) on the display device 50 including the exercise values 82 associated with the planned exercise sequence 76. In the illustrated embodiment, the computing device 16 determines the planned exercise sequence as a function of the retrieved patron record. In addition, the computing device 16 may determine a plurality of plurality of exercise values associated with the planned exercise sequence including, but not limited to, a number of exercise sets included in the current session, a number of exercise repetitions being included in each exercise set, a time to complete each exercise repetition, a tempo of exercise repetitions, a time to complete each set, and/or a time between each set.

In one embodiment, the computing device 16 determines a type of exercise device 14 being used by the patron 12 and selects a corresponding planned exercise sequence from the patron record. For example, in one embodiment, each exercise device 14 is associated with a unique device ID. Moreover, each sensor 20 that is coupled to an exercise device 14 may be configured to transmit a corresponding unique device ID upon sensing an exercise being performed using the corresponding exercise device 14. For example, in one embodiment, upon sensing a load being applied by the patron 12 to the weight bench 24, the first load sensor 34 and/or the second load sensor 36 may transmit a signal including an associated unique device ID to the computing device 16. The computing device 16 may receive a unique device ID from the sensors 34 and 36, determine an exercise device type being used by the patron as a function of the received unique device ID, and determine the planned exercise sequence as a function of the identified exercise device type. For example, the computing device 16 may identify the exercise device from a list of exercise device types contained in the database 70 as a function of the received unique device ID.

In method step 206, the computing device 16 receives sensed data indicative of an exercise sequence being performed by the patron with the exercise device 14. For example, in one embodiment, as the patron is performing an exercise using the weight bench 24, the computing device 16 may receive data indicative of a load being imparted on the exercise device 14 by the patron from the first and second load sensors 34 and 36. In addition, the computing device 16 may also receive data indicative of a position of the patron's body during the exercise. For example, as shown in FIG. 14, in one embodiment, the computing device 16 may receive video images of the patron's body from the video imaging device 38.

In method step 208, the computing device 16 determines a current exercise sequence being performed by the patron 12 as a function of the sensed data and displays information associated with the current exercise sequence. For example, in one embodiment, the computing device 16 may display fitness activity screens 90 (shown in FIGS. 8-12) that include information indicative of exercise values 82 associated with the current exercise sequence 74. Moreover, the computing device 16 may generate and display traces 72 corresponding to data indicative to the current exercise sequence 74 and the planned exercise sequences 76.

In the illustrated embodiment, the computing device 16 determines a plurality of exercise values associated with the current exercise session as a function of the sensed data. The exercise values may include, but are not limited to, a number of exercise sets included in the current session, a number of exercise repetitions being included in each exercise set, a time to complete each exercise repetition, a tempo of exercise repetitions, a time to complete each set, and a time between each set, a total effort, an average effort, a peak concentric force, an average concentric force, a peak eccentric force, and an average eccentric force.

Figure 9:
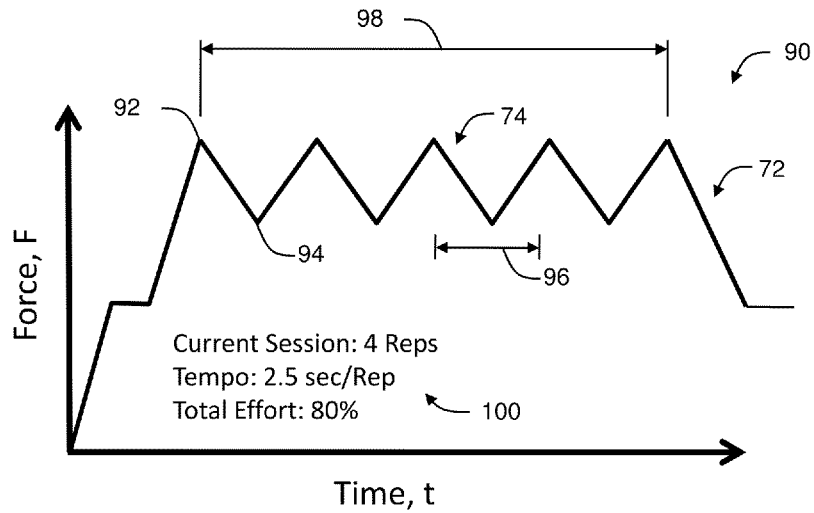
Figure 10:
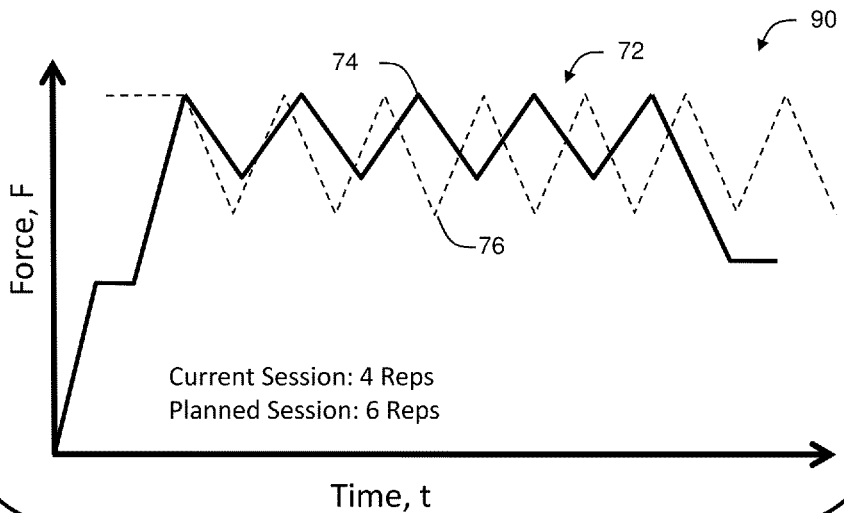
Figure 11:
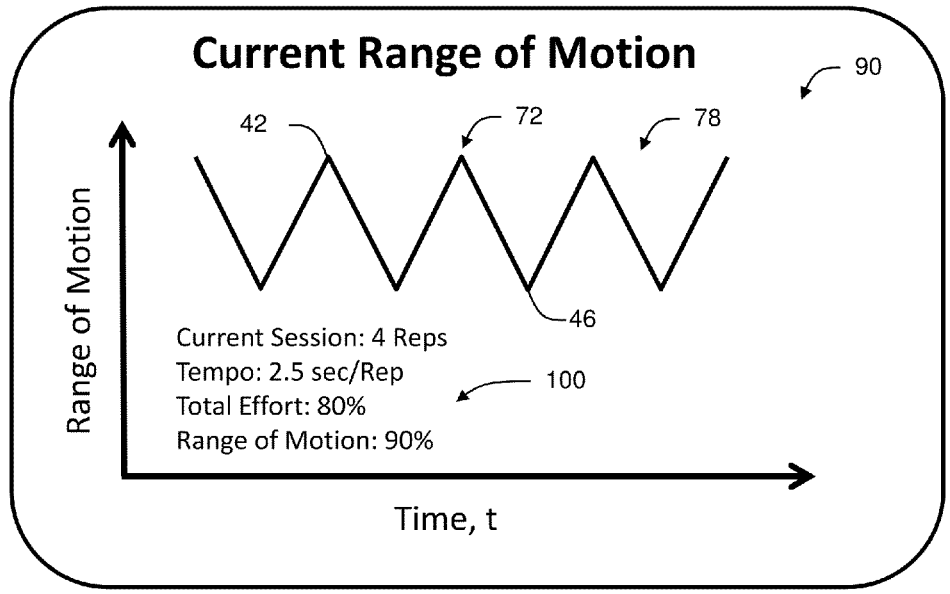
Figure 12:
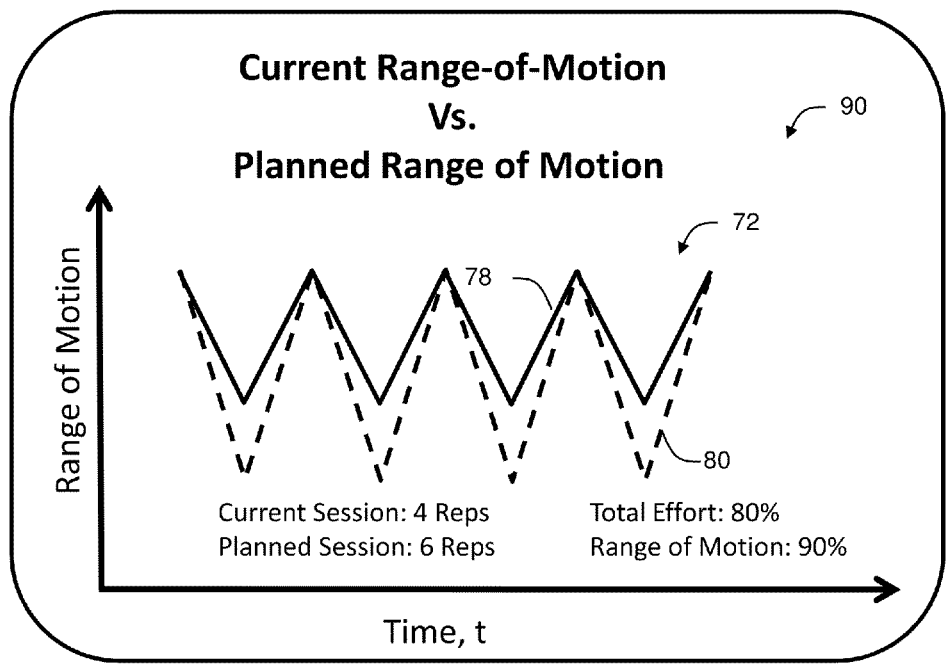

For example, referring to FIGS. 9 and 13, in one embodiment, the computing device 16 may determine that the patron is using the weight bench 24 to perform an exercise and retrieves a planned exercise sequence 76 from the corresponding patron record. The computing device 16 may also determine the planned exercise sequence to include a bench press exercise session including 4 sets of 6 repetitions. Each repetition including the lowering and raising of a weight bar by the patron. During the exercise session using the weight bench 24, the computing device 16 may receive sensed data including a force being applied to the exercise device 14 from the first and second load sensors 34 and 36. As the patron places weights on the weight rack 32, the computing device 16 senses and determines an amount of weight that will be lifted by the patron during the exercise based on the data received from the second load sensor 36. In addition, as the patron lifts the weight from the weight rack 32 to a first position 40 (shown in FIG. 13), the computing device 16 receives sensed data from the first load sensor 34 indicative of the full weight of the weights and patron being applied to the bench 30 and determines a maximum load 92 that is indicative of the patron being in the first position 40. As the patron lowers the weight towards the bench to a second position 44, the force being applied to the bench 30 is reduced. The computing device 16 senses a change in the force being applied to the bench 30, and determines a minimum load 94 that is indicative of the patron moving toward the second position 44. As the patron raises the weight to the first position 40, the force applied to the bench 30 increases towards the maximum load 92. As the patron 12 conducts a second repetition and moves towards the second position 44, the force applied to the weight bench 24 reduces, and the computing device 16 determines that the patron has completed a repetition 96 of the exercise. When the patron returns the weights to the weight rack 32, the computing device 16 receives a signal from the second load sensor 36 and determines that the patron has completed a set 98 of the exercise.

During the exercise session, the computing device 16 determines a number of repetitions 96 being performed by the patron as a function of the number of maximum and minimum loads detected by the sensors 20. In addition, the computing device 16 may determine a time to complete each repetition 96 and/or each set 98 as a function of the period of time between each sensed maximum load 92 and/or minimum load 94.

In one embodiment, the computing device 16 may determine a range of motion 78 being associated with the current exercise sequence and display the trace 72 including the determined range of motion 78. For example, referring to FIGS. 11 and 14, during an exercise, the computing device 16 may receive information from the video imaging device 38 that is indicative of the first position 40 including a first height 42 of the patron 12 in the first position 40. As the patron 12 moves from the first position 40 to the second position 44, the video imaging device 38 may transmit information indicative of a change in height from the first height 42 to a second height 46 of the patron 12 in the second position 44. Moreover, the computing device 16 may determine a range of motion 78 associated with the repetition 96 as a function of the sensed heights 42 and 46.

In method step 210, the computing device 16 determines a fitness activity of the patron as a function of the current exercise sequence and the planned exercise sequence. For example, in one embodiment, the computing device 16 may determine a condition of the patron exercise session as a function of the planned exercise sequence 76 and the current exercise sequence 74. Moreover, the computing device may determine the condition of the patron exercise session to be less than a predefined exercise session if the current exercise sequence is different from the planned exercise sequence, and responsively display a notification message on the display device. For example, in one embodiment, the planned exercise sequence may include a plurality of sets with each set including a predefined number of repetitions to be performed with a predefined period of time. The computing device 16 may compare the number of repetitions and the time to complete the set included with the current exercise sequence 74 and determine a level of fitness activity as a function of the differences between the number of repetitions performed with the current exercise sequence and the number of repetitions included in the planned exercise sequence.

In addition, the computing device 16 may calculate a total effort 100 associated with the fitness activity as a function of the current and the planned exercise sequences. For example, in one embodiment, the computing device 16 may calculate the percentage of planned repetitions being performed, a percentage of planned sets, a percentage of planned weight being lifted, and/or a percentage of planned duration of an exercise being performed by the patron and calculate the total effort 100 associated with the current exercise session as a function of the calculated percentages.

In method step 212, the computing device 16 generates a modified exercise sequence as a function of the current exercise sequence and the planned exercise sequence and stores the modified exercise sequence in the database for use during a subsequent exercise session initiated by the associated patron. For example, if the current exercise sequence includes 80% of the weight included in the planned exercise sequence, the computing device 16 may generate a modified exercise sequence that includes less weight and/or fewer repetitions than the previous planned exercise sequence.

The system 10 may also receive signals indicative of the position and/or the weight distribution of the patron and determine a spinal alignment and posture to indicate the body position is correct for the exercise being performed on the exercise device 14. For example, the computing device 16 may receive signals from the sensor pad 23 that are indicative of a weight distribution of the patron during an exercise. The system 10 may also receive motion-capture video images from the video imaging device 38 for use in determining if the patron's body is off balance, leaning, etc. Moreover, the system 10 may detect any unusual shift in weight with free weights used on the exercise device 14 while exercise device 14 and person are interacting and will display an alert massage on the user identification device 18, workstation 84, and/or display 54 to provide a notification that the athlete/patron may be in distress (especially necessary for unmanned workout facilities). Moreover, the system 10 may detect abnormal shifts in equipment being monitored and may also send alert messages to indicate potentially faulty equipment (safety feature).

While exemplary systems and methods in accordance with the invention have been described herein and in the accompanying materials, it should also be understood that the foregoing along with the accompanying materials are illustrative of a few particular embodiments as well as principles of the invention, and that various modifications can be made by those skilled in the art without departing from the scope and spirit of the invention. Therefore, the described embodiments should not be considered as limiting of the invention in any way. Accordingly, the invention embraces alternatives, modifications and variations which fall within the spirit and scope of the invention as set forth in the embodiments provided herein, and including equivalents thereto.

Although specific features of various embodiments of the invention may be shown in some drawings and not in others, this is for convenience only. In accordance with the principles of the invention, any feature of a drawing may be referenced and/or claimed in combination with any feature of any other drawing.

What is claimed is:

1. A system for monitoring a fitness activity of user performing a fitness activity with an exercise device, comprising:
   a sensor adapted to be coupled to the exercise device for sensing and transmitting data indicative of an exercise being performed with the exercise device, the sensed data including a force being applied to the exercise device;
   a user identification device for use in identifying a patron ID;
   a database including a collection of patron records, each patron record being associated with a corresponding patron ID and including a list of patron exercises; and
   a processor coupled to the sensor, the processor configured to:
   receive, from the sensor, a signal indicative of a force being applied to the exercise device and responsively initiate a patron exercise session;
   receive, from the user identification device, a signal indicative of a patron ID and responsively retrieve a patron record being associated with the received patron ID from the database;
   determine a planned exercise sequence associated with the patron exercise session as a function of the retrieved patron record;
   determine a current exercise sequence being performed by the patron with the exercise device as a function of the sensed force being applied to the exercise device; and
   determine a condition of the patron exercise session as a function of the planned exercise sequence and the current exercise sequence.

2. A system in accordance with claim 1, comprising a display device, the processor configured to determine the condition of the patron exercise session to be less than a predefined exercise session if the current exercise sequence is different from the planned exercise sequence, and responsively display a notification message on the display device.

3. A system in accordance with claim 2, the processor configured to generate and display a trace indicative of the planned exercise sequence and the current exercise sequence on the display device.

4. A system in accordance with claim 1, the processor configured to:
   determine a plurality of exercise values being associated with the current exercise sequence as a function of the sensed data; and
   generate and store data indicative of the current exercise sequence in the database, the current exercise sequence being associated with the patron record.

5. A system in accordance with claim 4, the plurality of exercise values including at least one of a number of exercise sets included in the current exercise sequence, a number of exercise repetitions being included in each exercise set, a time to complete each exercise repetition, a tempo of exercise repetitions, a time to complete each set, and a time between each set.

6. A system in accordance with claim 4, the plurality of exercise values including at least one of a total effort, an average effort, a peak concentric force, an average concentric force, a peak eccentric force, and an average eccentric force.

7. A system in accordance with claim 1, the processor configured to generate a modified exercise sequence as a function of the current exercise sequence and the planned exercise sequence and store the modified exercise sequence in the database for use during a subsequent exercise session initiated by the associated patron.

8. A system in accordance with claim 1, wherein the patron record includes a plurality of planned exercise sequences, each of the planned exercise sequences being associated with one of a plurality of exercise device types, the processor configured to:
   receive a unique device ID from the sensor;
   determine an exercise device type being used by the patron as a function of the received unique device ID; and
   determine the planned exercise sequence as a function of the identified exercise device type.

9. An apparatus for monitoring a fitness activity of user performing a fitness activity, comprising:
   an exercise device for use in performing the fitness activity by the user;
   a sensor coupled to the exercise device for sensing and transmitting data indicative of a fitness activity being perform with the exercise device, the sensed data including a force being applied to the exercise device;
   a user identification device for use in identifying a patron ID;
   a database including a collection of patron records, each patron record being associated with a corresponding patron ID and including a list of patron exercises; and
   a processor coupled to the sensor, the processor configured to:
   receive, from the sensor, a signal indicative of a force being applied to the exercise device and responsively initiate a patron exercise session;
   receive, from the user identification device, a signal indicative of a patron ID and responsively retrieve a patron record being associated with the received patron ID from the database;
   determine a planned exercise sequence associated with the patron exercise session as a function of the retrieved patron record;
   determine a current exercise sequence being performed by the patron with the exercise device as a function of the sensed force being applied to the exercise device; and
   determine a condition of the patron exercise session as a function of the planned exercise sequence and the current exercise sequence.

10. An apparatus in accordance with claim 9, comprising a display device, the processor configured to determine the condition of the patron exercise session to be less than a predefined exercise session if the current exercise sequence is different from the planned exercise sequence, and responsively display a notification message on the display device.

11. An apparatus in accordance with claim 10, the processor configured to generate and display a trace indicative of the planned exercise sequence and the current exercise sequence on the display device.

12. An apparatus in accordance with claim 9, the processor configured to:
   determine a plurality of exercise values being associated with the current exercise sequence as a function of the sensed data; and
   generate and store data indicative of the current exercise sequence in the database, the current exercise sequence being associated with the patron record.

13. An apparatus in accordance with claim 12, the plurality of exercise values including at least one of a number of exercise sets included in the current exercise sequence, a number of exercise repetitions being included in each exercise set, a time to complete each exercise repetition, a tempo of exercise repetitions, a time to complete each set, and a time between each set.

14. An apparatus in accordance with claim 12, the plurality of exercise values including at least one of a total effort, an average effort, a peak concentric force, an average concentric force, a peak eccentric force, and an average eccentric force.

15. An apparatus in accordance with claim 9, the processor configured to generate a modified exercise sequence as a function of the current exercise sequence and the planned exercise sequence and store the modified exercise sequence in the database for use during a subsequent exercise session initiated by the associated patron.

16. An apparatus in accordance with claim 9, wherein the patron record includes a plurality of planned exercise sequences, each of the planned exercise sequences being associated with one of a plurality of exercise device types, the processor configured to:
- receive a unique device ID from the sensor;
- determine an exercise device type being used by the patron as a function of the received unique device ID; and
- determine the planned exercise sequence as a function of the identified exercise device type.

17. A method for monitoring a fitness activity of user performing a fitness activity with an exercise device, including the steps of:
- receiving, by a processor, a signal indicative of a force being applied to the exercise device and responsively initiating a patron exercise session;
- receiving, from the user identification device, a signal indicative of a patron ID and responsively retrieving a patron record being associated with the received patron ID from a database;
- determining, a planned exercise sequence associated with the patron exercise session as a function of the retrieved patron record;
- determining a current exercise sequence being performed by the patron with the exercise device as a function of the sensed force being applied to the exercise device; and
- displaying a trace indicative of the planned exercise sequence and the current exercise sequence on a display device.

18. A method in accordance with claim 17, including the steps of:
- determining a plurality of exercise values being associated with the current exercise sequence as a function of the sensed data; and
- generating storing data indicative of the current exercise sequence in the database, the current exercise sequence being associated with the patron record.

19. A method in accordance with claim 17, including the steps of generating a modified exercise sequence as a function of the current exercise sequence and the planned exercise sequence and storing the modified exercise sequence in the database for use during a subsequent exercise session initiated by the associated patron.

20. A method in accordance with claim 17, wherein the patron record includes a plurality of planned exercise sequences, each of the planned exercise sequences being associated with one of a plurality of exercise device types, the method including the steps of:
- receiving a unique device ID from the sensor;
- determining an exercise device type being used by the patron as a function of the received unique device ID; and
- determining the planned exercise sequence as a function of the identified exercise device type.

\* \* \* \* \*